United States Patent [19]

Tawfik

[11] 4,203,929
[45] May 20, 1980

[54] GEM DICHLOROCYCLOPROPANES AND METHOD OF MAKING SAME

[76] Inventor: Sobhy Tawfik, 89-15 102nd St., Richmond Hill, N.Y. 11418

[21] Appl. No.: 915,920

[22] Filed: Jun. 16, 1978

[51] Int. Cl.$^2$ ............................................. C07C 17/28
[52] U.S. Cl. ............................ 260/648 D; 260/648 R
[58] Field of Search ........................ 260/648 R, 648 D

[56] References Cited
PUBLICATIONS

Chem. Abs. 67, 53734.
Chem. Abs. 67, 43094.
Chem. Abs. 66, 65182.
Chem. Abs. 81, 15187 & 15188.

*Primary Examiner*—C. Davis

[57] ABSTRACT

Gem dichlorocyclopropanes are prepared by the reaction of a butene with chloroform in the presence of cetyl trimethyl ammonium bromide as catalyst.

1 Claim, No Drawings

GEM DICHLOROCYCLOPROPANES AND METHOD OF MAKING SAME

The present invention relates to the production of Gem-Dichlorocyclopropanes. More particularly it relates to the generation of carbene in the presence of an acceptor substance. It further relates to the contact of carbene with an acceptor substance in the liquid phase and under atmospheric pressure.

Gem-Dichlorocyclopropanes are important as pharmaceuticals, hopefuly cancer remedy, as fragrances, essence, cosmetics, insecticides and oils. The idea that salts might have a significant solubility in organic phases is relatively strange to the preparative organic chemist. Typical ionic compounds are frequently extracted from aqueous solution into organic solvents in the form of ion pairs. With suitable solvents it is possible to extract the salts of most amines in almost quantitative yield. Tertiary amines are more readily extracted than their secondary or primary amines. A high molecular weight and absence of hydrophilic groups favor extraction.

In the same way as alkylammonium salts of inorganic acids, the salts of weak organic acids can also be extracted and obtained in crystalline form. Generation of dichlorocarbene from aquous sodium hydroxide, ammonium salt, and haloform can be interpreted as:

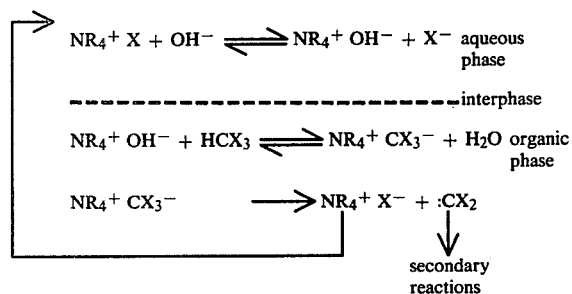

Small ions e.g. tetramethylammonium are not suitable as catalysts. In contrast, large ions tetrabutylammonium and tetradodecylammonium ions are very effective, regardless of their molecular shape.

The mixing speed has no influence on the reaction kinetics once a limiting value for thorough mixing has been reached.

Formerly dihalocarbenes were generally assumed to be exceptionally sensitive to moisture, since chloroform is known to undergo hydrolysis to formate. However, the carbene formed by the phase transfer technique undergoes further reaction so rapidly that it is hardly hydrolysed. This would contraindicate formation of the major portion of the carbene at the interface.

By way of illustration 2,3-Dimehtyl-2-butene reacted in the liquid phase with dichlorocarbene generated therein i.e.

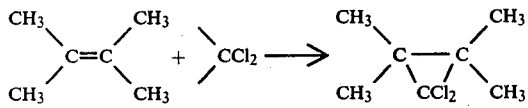

1,1-Dichloro-2,2,3,3,-tetramethylcyclopropane was the product of this operation.

Owing to simplicity and low cost of the reagents the method of the present invention should soon find universal application, not least in many technical processes.

Where Gem-Dichlorocyclopropane is produced in the liquid phase from a mixture of chloroform, olefin, sodium hydroxide solution and Cetrimide, it is preferred that the reactants be in the proportion of chloroform from 0.07 to 0.14 mole, olefins from 0.17 to 0.34 mole, 50% sodium hydroxide from 0.43 to 0.86 mole NaOH and cetrimide from 0.0025 to 0.005 mole and the reaction temperature from $-7°$ C. to $40°$ C. for the first 0.5 hour. After the addition is complete, the reaction mixture is stirred at room temperature for 1-2 hours. The organic layer is separated and washed with water (two 50-100 ml. portions).

The last wash gives an emulsion which is broken by the addition of from 2.5 to 5 ml. of saturated sodium chloride solution. Analysis of the organic layer by G.L.C. follows.

Verification of the reaction products is by mass spectrograph. Separation of the components is by vacuum distillation through Vigreux column.

EXAMPLE I

Chloroform 9.14 grams, 0.07 mole was added to a stirred mixture of 2,3-Dimethyl-2-butene 14.9 grams, 0.17 mole, 50% sodium hydroxide solution 35 grams, 0.43 mole and Cetrimide 0.9 grams (Cetyltrimethylammonium bromide main component), 0.0025 mole at such a rate that the temperature was maintained at $30°-40°$ C. about 0.5 hour.

After the addition was complete the reaction mixture was stirred at room temperature for one hour.

The organic layer was separated and washed with water (two 50 ml. portions). The last wash gave an emulsion which was broken up by the addition of 2.5 ml. of saturated sodium chloride solution.

Analysis of the organic layer showed it to contain 13.8 grams of 1,1-Dichloro-2,2,3,3-tetramethylcyclopropane equivalent to 100 area percent as demonstrated by G.L.C. and the m.p. of the crystalline needles $53°$ C.

EXAMPLE II

The procedure of example I was repeated using 2-Methyl-2-butene as the substrate.

The operation gave an organic layer which by analysis showed it to contain 4.5 grams of 1,1-Dichloro-2,2,3-trimethylcyclopropane equivalent to 100 area percent as demonstrated by G.L.C. The product fraction obtained by vacuum distillation through a Vigreux column and its b.p. $145°$ C. at atmospheric pressure.

EXAMPLE III

The procedure of example I was repeated using 2-Methylpropene as the substrate.

The operation gave an organic layer which by analysis showed it to contain 1.5 grams of 1,1-Dichloro-2,2-dimethylcyclopropane equivalent to 100 area percent as demonstrated by G.L.C. The product fraction obtained by vacuum distillation through a Vigreux column and its b.p. $119°$ C. at atmospheric pressure.

EXAMPLE IV

The procedure of example I was repeated using Cis-2-butene as the substrate.

The operation gave an organic layer which by analysis showed it to contain 1.3 grams of 1,1-Dichloro-2,3-cis-dimethylcyclopropane equivalent to 100 area percent as demonstrated by G.L.C. The product fraction obtained by vacuum distillation through a Vigreux column and its b.p. 130° C. at atmospheric pressure.

EXAMPLE V

The procedure of example I was repeated using Trans-2-butene as the substrate.

The operation gave an organic layer which by analysis showed it to contain 5.8 grams of 1,1-Dichloro-2,3-trans-dimethylcyclopropane equivalent to 100 area percent as demonstrated by G.L.C. The product fraction obtained by vacuum distillation through a Vigreux column and its b.p. 123° C. at atmospheric pressure.

EXAMPLE VI The procedure of example I was repeated using 1-Butene as the substrate.

The operation gave an organic layer which by analysis showed it to contain 0.4 grams of 1,1-Dichloro-2-ethylcyclopropane equivalent to 100 area percent as demonstrated by G.L.C. The product fraction obtained by vacuum distillation through a Vigreux column and its b.p. 126° C. at atmospheric pressure.

EXAMPLE VII

The procedure of example I was repeated using 3-Methyl-1-butene as the substrate.

The operation gave an organic layer which by analysis showed it to contain 1.3 grams of 1,1-Dichloro-2-isopropylcyclopropane equivalent to 100 area percent as demonstrated by G.L.C. The product fraction obtained by vacuum distillation through a Vigreux column and its b.p. 139° C. at atmospheric pressure.

I claim:

1. The method of making gem dichlorocyclopropane comprising reacting 2,3-dimethyl-2-butene with chloroform in liquid phase by phase transfer catalysis in the presence of cetyl trimethyl ammonium bromide in a sodium hydroxide solution at a temperature of −7° to 40° C.

* * * * *